(12) United States Patent
Matsui et al.

(10) Patent No.: US 6,642,432 B1
(45) Date of Patent: Nov. 4, 2003

(54) COMPRESSION RECOVERY SHEET, PRODUCTION PROCESS THEREOF AND ABSORBENT ARTICLE CONTAINING THE SAME

(75) Inventors: Manabu Matsui, Tochigi-ken (JP); Tetsuya Masuki, Tochigi-ken (JP); Manabu Kaneda, Tochigi-ken (JP); Takanobu Miyamoto, Tochigi-ken (JP); Akihiko Gunji, Tochigi-ken (JP); Mikio Suzuki, Tochigi-ken (JP); Taiki Uchiyama, Tochigi-ken (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/610,472

(22) Filed: Jul. 5, 2000

(30) Foreign Application Priority Data

| Jul. 5, 1999 | (JP) | 11-190969 |
| Jul. 5, 1999 | (JP) | 11-190970 |
| Dec. 28, 1999 | (JP) | 11-373961 |

(51) Int. Cl.$^7$ .................................................. A61F 13/15
(52) U.S. Cl. ........................ 604/380; 604/379; 604/383
(58) Field of Search ............................... 604/358, 365, 604/366, 367, 369, 370, 371, 372, 375, 379, 380, 385.09, 385.23; 442/171, 361–365, 408

(56) References Cited

U.S. PATENT DOCUMENTS

| 4,798,603 A | * | 1/1989 | Meyer et al. | 604/378 |
| 5,128,082 A | * | 7/1992 | Makoui | 264/112 |
| 5,336,552 A | * | 8/1994 | Strack et al. | 428/224 |
| 5,382,400 A | * | 1/1995 | Pike et al. | 264/168 |
| 5,522,810 A | * | 6/1996 | Allen, Jr. et al. | 604/366 |
| 5,649,916 A | * | 7/1997 | DiPalma et al. | 604/378 |
| 5,846,230 A | * | 12/1998 | Osborn, III et al. | 604/378 |
| 5,849,001 A | * | 12/1998 | Torimae et al. | 604/372 |
| 5,858,528 A |   | 1/1999 | Tashiro et al. | |
| 5,859,074 A | * | 1/1999 | Rezai et al. | 521/54 |
| 5,964,743 A | * | 10/1999 | Abuto et al. | 604/385.1 |
| 6,034,005 A | * | 3/2000 | Diehl | 442/164 |
| 6,264,872 B1 | * | 7/2001 | Majors et al. | 264/384 |
| 6,310,163 B1 | * | 10/2001 | Brookhart et al. | 526/318.6 |

FOREIGN PATENT DOCUMENTS

| EP | 0483386 A1 | 5/1992 | |
| EP | WO9616624 | 6/1996 | |
| GB | 1202958 | 8/1970 | |
| GB | 2227174 A | 7/1990 | |
| JP | 61106151 | 5/1986 | |
| JP | 1285265 | 11/1989 | A61F/13/18 |
| JP | 5161525 | 6/1993 | A47C/27/12 |
| JP | 7316963 | 5/1995 | D04H/1/54 |

OTHER PUBLICATIONS

Nonwovens. com—"Binder Classifications", Types of Nonwoven Binder, "Thermal Bonding Process"—1999—Source—World Wide Web.*

* cited by examiner

Primary Examiner—Weilun Lo
Assistant Examiner—Jacqueline F Stephens
(74) Attorney, Agent, or Firm—Birch, Stewart, Kolasch & Birch, LLP (57) ABSTRACT

A compression recovery sheet which comprises a fiber aggregate containing 10 to 90% by weight of an elastomeric component and has a basis weight of 15 to 100 g/m$^2$, a no-load thickness of 1 to 10 mm, and a compressive recovery of 60% or more and an absorbent article containing the same are disclosed.

18 Claims, 4 Drawing Sheets

COMPRESSION RECOVERY SHEET, PRODUCTION PROCESS THEREOF AND ABSORBENT ARTICLE CONTAINING THE SAME

BACKGROUND OF THE INVENTION

The present invention relates to a compression recovery sheet which is lightweight, bulky and thin and has high compression recovery properties, a process for producing the same, and an absorbent article containing the same. More particularly, the present invention relates to a compression recovery sheet such as may be used as a constituent member to provide an absorbent article, etc., such as a disposable diaper and a sanitary napkin, that is thin in a packaged state (under some load) but recovers thickness on being taken out of the package (on removal of the load) to gain a sufficient thickness required of the absorbent article, etc. enough to give users a feeling of assurance, a process for producing the same, and an absorbent article containing the same.

The recent absorbent articles such as disposable diapers and sanitary napkins have been made more compact and easier to carry in packages by improvements added to the structure and the material. However, if absorbent articles such as disposable diapers are made thinner to make the package more compact, the absorbent article lacks stiffness and makes a user feel a fear of leakage during use. Therefore, it has been demanded to develop absorbent articles which are compact and light in their packaged state but restore their thickness when taken out of the package for use thereby giving a user a feeling of assurance while worn.

In order to eliminate the fear of leaks during use, it has been proposed to use a fiber aggregate, such as nonwoven fabric made of polyester fiber or thermally fusible fiber or a mixed sheet of these fibers and pulp as a cushioning layer in absorbent articles. Such fiber aggregates include those described in Japanese Patent Laid-Open Publication Nos. 61-106151 and 1-285265. For example, the Publication No. 1-285265 discloses an absorbent article having an elastic member of a fiber aggregate mainly comprising synthetic fiber under an absorbent member. The subject matter of the invention disclosed resides in disposing nonwoven fabric formed of synthetic fiber having high elasticity under an absorbent member to absorb the stress imposed on the absorbent member and to secure recovery properties thereby to prevent leakage. However, the fiber aggregates according to these publications fail to perform the function as a cushioning layer of an absorbent article in actual use or after relief from a highly compressed state, for example, a packaged state.

Use of a fiber aggregate comprising an elastomeric component as a cushioning material has also been proposed in the fields other than absorbent articles, such as furniture, beds, seats, and the like (see Japanese Patent Laid-Open Publication Nos. 5-161525 and 7-316963). However, the fiber aggregates proposed as a cushioning material have, in nature of the purpose of use, a very large basis weight and a large thickness not smaller than 5 mm, practically 50 mm or greater. For these reasons and for the economical consideration, they are inapplicable to absorbent articles. Although urethane foam could be a conceivable cushioning material of an absorbent article, it is unacceptable because of not only high cost incurred but yellowing and smell.

SUMMARY OF THE INVENTION

An object of the present invention is to provide a compression recovery sheet which is thin in a packaged state (under some load) but restores thickness on being taken out of the package (on removal of the load) to gain a sufficient thickness required of an absorbent article, etc. enough to make a user feel assured, a process for producing the same, and an absorbent article containing the same.

Another object of the present invention is to provide a compression recovery sheet which is suited for use as a cushioning material of furniture, beds, seats, and the like.

The present invention provides a compression recovery sheet which comprises a fiber aggregate containing 10 to 90% by weight of an elastomeric component and has a basis weight of 15 to 100 g/m$^2$, a no-load thickness of 1 to 10 mm, and a compressive recovery of 60% or more.

The present invention also provides a compression recovery sheet which comprises a fiber aggregate substantially comprising synthetic fiber and having been impregnated or coated with an adhesive whose glass transition temperature is 4° C. or lower and has a basis weight of 15 to 100 g/m$^2$, a no-load thickness of 1 to 10 mm, and a compressive recovery of 60% or more.

The present invention further provides a preferred process for producing the above-described compression recovery sheet, which comprises heat treating a fiber aggregate web to form a fiber aggregate sheet and heat rolling the sheet with an engraved roll.

The present invention furthermore provides an absorbent article comprising a liquid permeable topsheet, a liquid-impermeable leakproof sheet, a liquid retentive absorbent member interposed between the topsheet and the leakproof sheet and, as a cushioning member, the above-described compression recovery sheet.

BRIEF DESCRIPTION OF THE DRAWINGS

The present invention will be more particularly described with reference to the accompanying drawings, in which.

DETAILED DESCRIPTION OF THE PREFERRED EMBODIMENT

The compression recovery sheet of the present invention will be described in detail with reference to preferred embodiments thereof.

The compression recovery sheet according to a first embodiment of the present invention comprises a fiber aggregate containing 10 to 90% by weight, preferably 15 to 60% by weight, of an elastomeric component. If the proportion of the elastomeric component is less than 10% by weight, sufficient compressive recovery cannot be obtained. If it exceeds 90% by weight, it is difficult to make the fiber aggregate into a sheet form, and the cost increases for only a slight improvement of compressive recovery.

The elastomeric component includes thermoplastic elastomers of ester type, urethane type, olefin type, styrene type or amide type. Inter alia, polyesters and low-density polyethylene produced by polymerization in the presence of a metallocene catalyst are preferred. The polymer constituting the elastomeric component can contain various stabilizers, ultraviolet absorbers, thickening and branching agents, delusterants, colorants, and other modifiers.

It is preferred that the fiber aggregate of this embodiment comprises conjugate fiber composed of an elastomeric component and a non-elastomeric component from the viewpoint of the compression recovery properties of the resulting sheet and firm thermal fusibility of fibers in sheet making.

The elastomeric component of the conjugate fiber includes those enumerated above. The non-elastomeric component of the conjugate fiber includes polyesters, such as polyethylene terephthalate (PET) and polybutylene terephthalate (PBT), polyolefins, such as polyethylene (PE) and polypropylene (PP), nylon, and acrylic resins. The polymer constituting the non-elastomeric component can contain various stabilizers, ultraviolet absorbers, thickening and branching agents, delusterants, colorants, and other modifiers.

The proportion of the conjugate fiber in the fiber aggregate is preferably 10 to 90% by weight, still preferably 30 to 70% by weight. The weight ratio of the elastomeric component to the non-elastomeric component in the conjugate fiber is preferably 80/20 to 20/80, still preferably 60/40 to 40/60.

Figure 1:
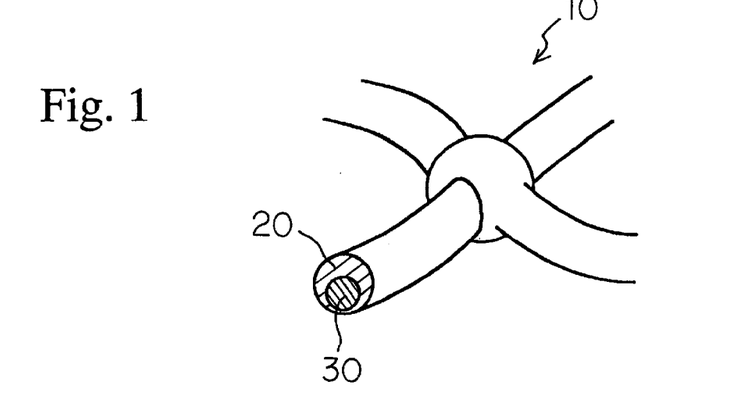
FIG. 1 is a schematic perspective view showing the cross section of a conjugate fiber as an example of fibers making up a fiber aggregate of the compression recovery sheet according to the present invention.

The configuration of the conjugate fiber includes a side-by-side form, a core-sheath form, an eccentric core-sheath form, a sea-island form. In particular, a core-sheath form, especially an eccentric core-sheath form as shown in FIG. 1 is preferred, in which a conjugate fiber 10 has a non-elastomeric component 30 as a core and an elastomeric component 20 as an outer sheath. The fibers making up the fiber aggregate are preferably bonded to each other by thermal fusion, and the like as depicted in FIG. 1.

The other fiber making up the fiber aggregate in conjunction with the conjugate fiber may be made of either the above-described elastomeric component or the above-described non-elastomeric component.

The shape of the fibers constituting the fiber aggregate is not particularly limited and includes, for example, a mechanical two-dimensionally crimped form, a three-dimensionally crimped form (in a helical form), and a mixed form thereof. The section of the fibers constituting the fiber aggregate includes, but is not limited to, a circular shape, a flattened shape, an odd shape, and a hollow shape. The fineness (thickness) of the fibers is preferably 1 to 15 denier, still preferably 2 to 10 denier.

In the present embodiment, it is preferred that the fiber aggregate contains 10% by weight or more, particularly 30% by weight or more, of crimped fibers of helical form so that the sheet may have bulkiness, stiffness and improved compression recovery properties. The crimped fibers of helical form may be of the conjugate fibers, the fibers comprising the elastomeric component, or the fibers comprising the non-elastomeric component.

The number of crimps of the crimped fibers is obtained in accordance with JIS L1015. The test of JIS L1015 is summarized as follows: On glossy and smooth paper on which sectioning lines have been drawn, fix one by one the samples which are sampled from several parts where crimps are intact, preserved at both ends with adhesives in the manner to let the fiber have 25±5% looseness to the strip in each of the sections. For the adhesives, select suitable adhesive according to the kind of fiber, which shall give no damage to the fiber. Attach each of these fibers at the grips of a crimp tester, and, after cutting the strip, read the distance between the grips (spacing distance) and count the number of crimps under loading pretension, and obtain the number of crimps. Repeat for 20 times and average the value for the number of crimps.

The number of crimps (as measured in accordance with JIS L1015) of the crimped fibers of helical form is preferably 3 to 20, still preferably 5 to 15, per inch. The crimped fibers of helical form can be obtained by known techniques. For example, eccentric core-sheath conjugate fibers composed of two components having different thermal shrinkage percentages are subjected to heat treatment.

The fibers other than the crimped fibers of helical form in the fiber aggregate can be mechanical two-dimensionally crimped fibers.

While the fiber aggregate is preferably one containing conjugate fibers comprising an elastomeric component and a non-elastomeric component, especially core-sheath conjugated fibers or eccentric core-sheath conjugate fibers, as stated above, it may be one composed of non-conjugate fibers, i.e., fibers made of the above-described elastomeric component or fibers made of the above-described non-elastomeric component, or one composed of the conjugate fibers and the non-conjugate fibers.

The configuration of the fiber aggregate includes dry-processed nonwoven fabric, wet-processed nonwoven fabric, woven fabric, knitted fabric, and composite sheets thereof.

The fiber aggregate includes not only the one made up solely of the above-described elastomeric and/or non-elastomeric fibers but a sheet comprising the above-described fibers and pulp, such as wood pulp (e.g., cotton-like pulp and comminuted pulp), natural fiber (e.g., cotton), regenerated fiber (e.g., rayon), and the like. These other fibers such as pulp is preferably used in the fiber aggregate in a proportion of 5 to 70% by weight, particularly 10 to 50% by weight.

The fiber aggregate may be used in the form of a composite sheet with a pulp sheet, a film, a foamed sheet, and the like.

The compression recovery sheet according to the present embodiment has a basis weight of 15 to 100 g/m$^2$, preferably 20 to 80 g/m$^2$. If the basis weight is less than 15 g/m$^2$ it is difficult for the sheet to exert sufficient compressive recovery due to lack of fiber denseness. If the basis weight exceeds 100 g/m$^2$, the resulting absorbent article is uncompetitive in price and no more lightweight nor compact when packaged.

The compression recovery sheet according to the present embodiment has a no-load thickness of 1 to 10 mm, preferably 1.2 to 5 mm. A sheet thinner than 1 mm is too flimsy to give a thickness feeling and to produce a cushioning effect. A sheet thicker than 10 mm is so bulky and, when used in a absorbent article such as a disposable diaper, the resulting disposable diaper would be so thick as to be inconvenient to fit to a wearer's body, or a package containing a plurality of such disposable diapers would be, being so large, inconvenient to carry. With the above no-load thickness, the compression recovery sheet can preferably be compressed to a thickness of 0.2 to 3 mm, particularly 0.3 to 1 mm. The term "no-load thickness" as used herein means the thickness of the sheet measured after being allowed to stand for 24 hours with no load applied to remove any strain that may have been imposed to the sheet. The no-load thickness is obtained as an average measured with a laser displacement sensor PA-1830, supplied by Keyence Corp., in a usual manner.

The compression recovery sheet of the present invention has a compressive recovery of 60% or more, preferably 70 to 100%, still preferably 80 to 100%, particularly preferably 90 to 100%. If the compressive recovery is less than 60%, the sheet is incapable of providing an absorbent article, such as a disposable diaper, that is sufficiently thin in a package and yet, on use, secures a thickness enough to give a user a feeling of assurance. The compressive recovery can be measured as follows.

Method of Compressive Recovery Measurement:

The thickness of a sheet after being allowed to stand for 24 hours under no load (the thickness before compression) is taken as a (mm). The thickness of the sheet after being compressed under a load of 180 gf/cm$^2$ for 24 hours and then, after the load is removed, allowed to stand for 30 minutes is taken as b (mm). Compressive recovery is defined to be b/a×100 (%). Thickness measurement is made with a laser displacement sensor PA-1830, supplied by Keyence Corp., and an average is obtained in a usual manner.

Figure 2:
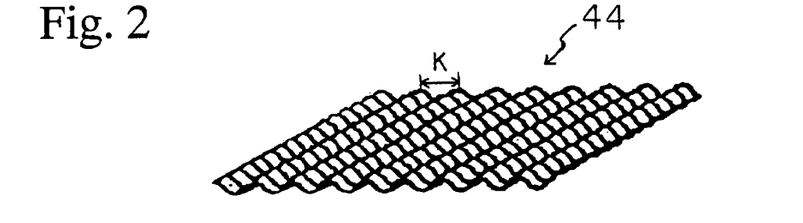
FIG. 2 is a perspective view of an example of the compression recovery sheet according to the present invention.

As shown in FIG. 2, the compression recovery sheet 44 according to the present embodiment preferably has a large number of bosses (projections) regularly arrayed. The compression recovery sheet 44 has on one side thereof a large number of regularly arrayed bosses and on the reverse side the corresponding depressions in such a manner that the contour of the face side and that of the back side are substantially the same.

The number of bosses is preferably 1 to 100, still preferably 1.5 to 50, per cm$^2$ of the projected area of the compression recovery sheet (the area in its plan view). The pitch K of the bosses (the center-to-center distance between bosses, see FIG. 2) is preferably 1 to 20 mm, still preferably 1 to 10 mm.

Figure 3A:
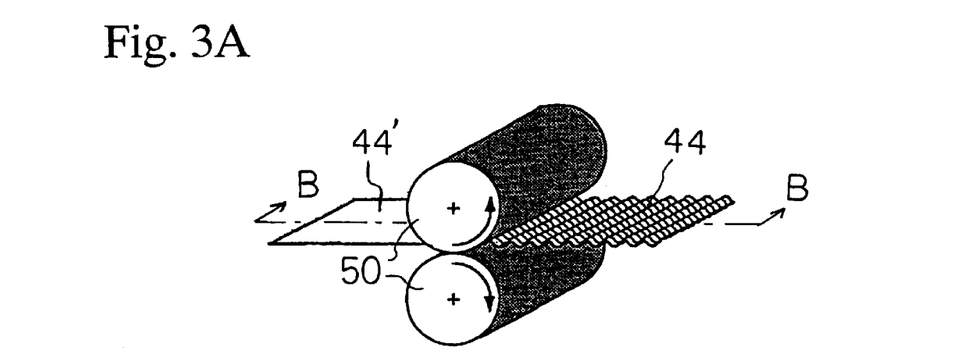
FIG. 3A is a schematic perspective view illustrating part of the apparatus used to produce the compression recovery sheet of FIG. 2.
Figure 3B:
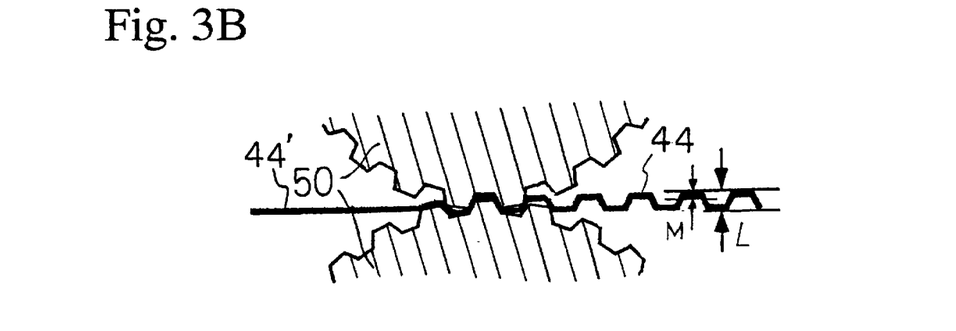
FIG. 3B is an enlarged cross sectional view, taken along line B—B of FIG. 3A.

Such an uneven pattern composed of a great number of bosses can be formed by, for example, passing a sheet 44' of the fiber aggregate through a matched pair of relief engraved heat rolls 50 and 50, such as matched-steel emboss rolls as are illustrated in FIGS. 3A and 3B.

The height L of the bosses (see FIG. 3B) is practically equal to the no-load web thickness of the compression recovery sheet.

The thickness M shown in FIG. 3B, the distance between the face and the back of the compression recovery sheet, is preferably 0.05 to 1 mm, still preferably 0.1 to 0.8 mm. The thickness M is almost uniform throughout the entire area of the sheet.

The compression recovery sheet according to the above-described embodiment is produced by, for example, a process comprising blending conjugated fiber composed of an elastomeric component and a non-elastomeric component with fiber comprising an elastomeric component and/or fiber comprising a non-elastomeric component, these fibers being prepared in a conventional manner by melt spinning, gel spinning, and the like, and, if desired, adding pulp fiber, etc., carding and making the fiber blend into a web by means of a carding machine, and making the web into a sheet by, for example, subjecting the web to a heat treatment. If necessary, the resulting sheet is subjected to the above-mentioned heat roll processing by means of a relief engraved roll.

Figure 4:
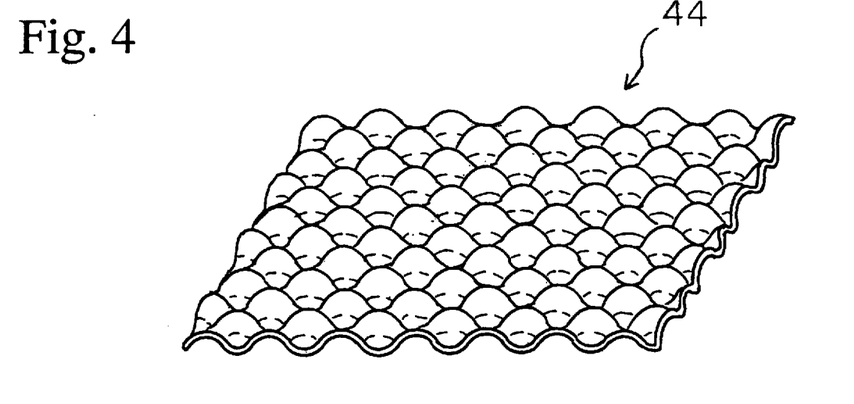
FIG. 4 is a perspective view of another example of the compression recovery sheet according to the present invention.

Another preferred example of the compression recovery sheet according to the present invention is shown in FIG. 4. The shape of the compression recovery sheet of the present invention is not limited to a flat shape as has been illustrated in FIGS. 2 and 4 and may be shaped to have a curved surface according to the use. Further, the embossed pattern on one side and that of the reverse side may be different.

The compression recovery sheet according to another preferred embodiment of the present invention comprises resin-bonded nonwoven fabric having a basis weight of 15 to 100 g/m$^2$, a no-load thickness of 1 to 10 mm, and a compressive recovery of 60% or more, the resin-bonded nonwoven fabric being a fiber aggregate web substantially comprising synthetic fiber and having been impregnated or coated with an adhesive whose glass transition temperature is 4° C. or lower. The description about the aforementioned first embodiment applies to this second embodiment except the following points. The term "substantially" as used herein about the composition of the fiber aggregate is intended to mean that the fiber aggregate may contain, in addition to synthetic fiber, natural fiber (e.g., cotton, wool or flax), regenerated fiber (e.g., rayon or cuprammonium rayon), and the like. The proportion of the fibers other than synthetic fiber in the fiber aggregate is preferably 10 to 70% by weight, still preferably 20 to 50% by weight based on the weight of the fiber aggregate.

The synthetic fiber typically includes polypropylene fiber, polyethylene terephthalate fiber, and a mixture thereof. Because preparation of the resin-bonded nonwoven fabric involves a heat treatment at 130 to 170° C. to evaporate water from an emulsion type adhesive as hereinafter described, it is preferred to use synthetic fiber that does not melt in this temperature range. Such fiber includes polyethylene terephthalate fiber.

It is preferred for the synthetic fiber to have a fiber diameter of 3 to 20 dtex, particularly 5 to 15 dtex to secure satisfactory compression recovery properties. The synthetic fiber can be used in the form of either a continuous filament or a staple fiber. The fiber aggregate substantially comprising the synthetic fiber is formed by, for example, carding staple fibers.

The adhesive with which the fiber aggregate web is impregnated or coated has a glass transition temperature (hereinafter "Tg") of 4° C. or lower, preferably −4° C. or lower.

By using an adhesive whose Tg is 4° C. or lower, sufficient compression recovery properties are imparted to the fiber aggregate web.

Tg is obtained from the following Fox's equation (see Nenchaku Handbook, p. 144, Nippon Nenchaku Tape Kogyokai (Dec. 12, 1995) and Japanese Patent 2,886,686, col. 7).

$$\frac{\sum_i W_i}{Tg} = \sum_i \frac{W_i}{Tg_i}$$

wherein Tg is a glass transition temperature (° K) of an adhesive; $Tg^i$ is a glass transition temperature (° K) of monomer i; and $W_i$ is a weight fraction of monomer i.

The adhesive which can be used in this embodiment includes emulsion type adhesives comprising an acrylic ester as a base polymer, vinyl acetate adhesives, acrylic/vinyl acetate adhesives, styrene/acrylic adhesives, polyester adhesives, and urethane adhesives. The acrylic ester-based emulsion type adhesives which have a sufficiently low Tg are particularly preferred.

It is preferred to offer sheet strength and sufficient compression recovery properties that the resin-bonded nonwoven fabric contains the adhesive in an amount of 10 to 60% by weight, particularly 15 to 50% by weight based on the weight of the resin-bonded nonwoven fabric.

Impregnation or coating of the fiber aggregate web with the adhesive is carried out by dipping the fiber aggregate web in the adhesive or spraying the adhesive onto the fiber aggregate web.

The compression recovery sheet according to the present invention is primarily suited as a cushioning member of absorbent articles, such as disposable diapers of unfolded type or folded type (pants type), sanitary napkins, and incontinence pads, and also useful as a cushioning material of furniture, beds, seats, pads, shoe-socks, and the like.

Figure 5:
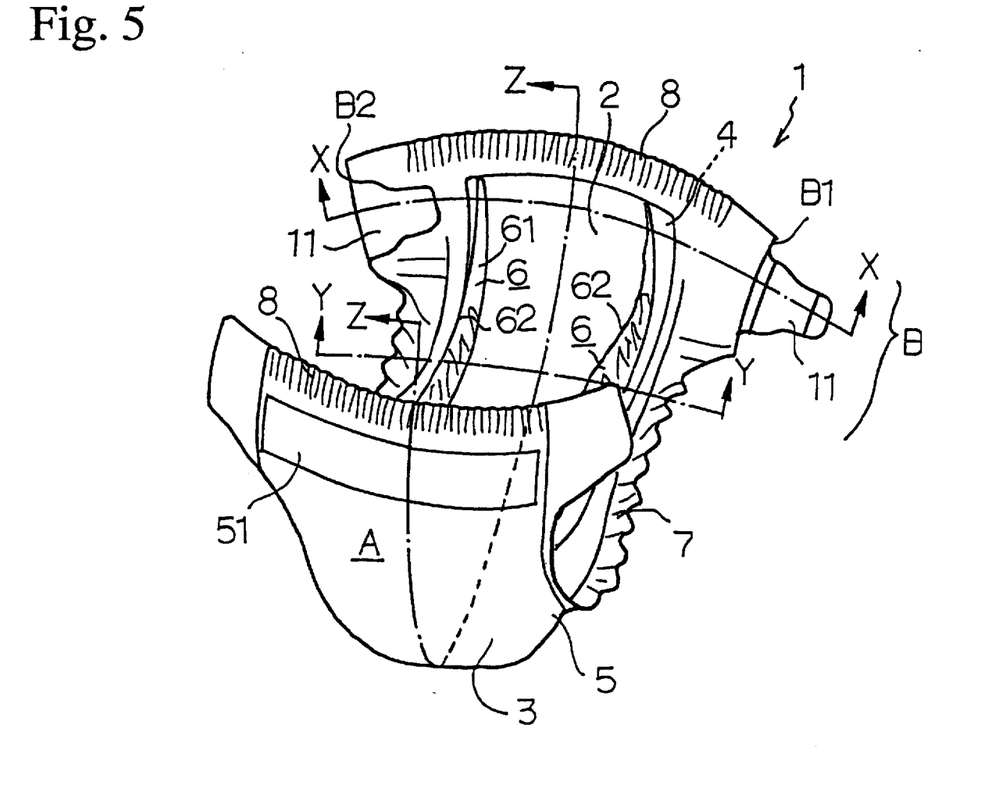
FIG. 5 is a perspective view depicting an embodiment of a disposable diaper as an absorbent article of the present invention.
Figure 6:
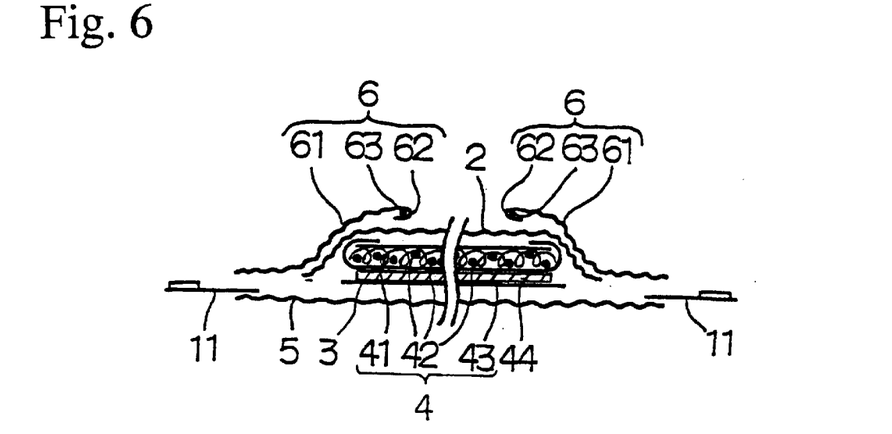
FIG. 6 is a schematic cross sectional view, taken along X—X line of FIG. 5.
Figure 7:
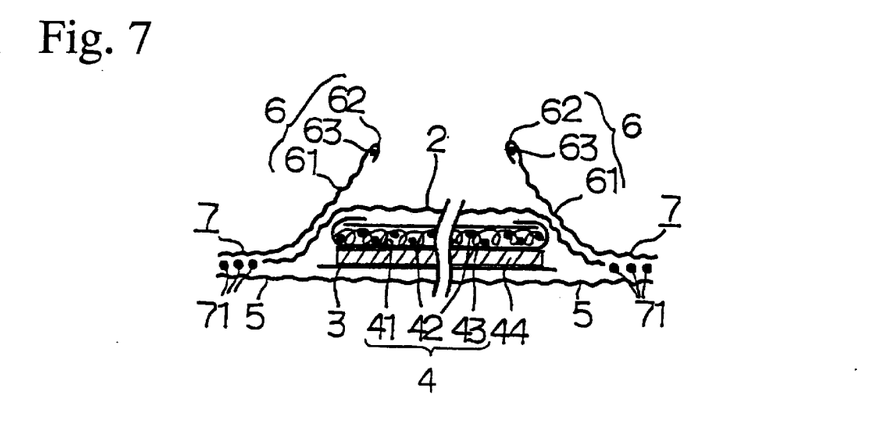
FIG. 7 is a schematic cross sectional view, taken along Y—Y line of FIG. 5.
Figure 8:
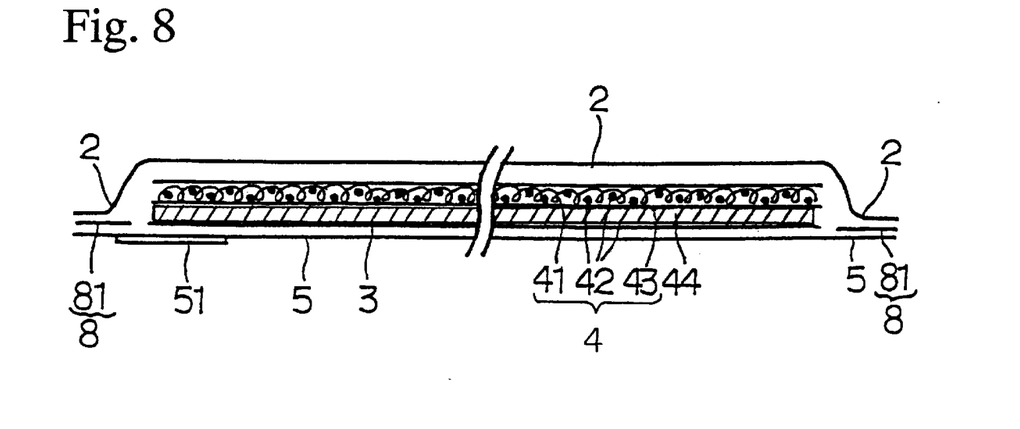
FIG. 8 is a schematic cross sectional view, taken along Z—Z line of FIG. 5.

The absorbent article according to the present invention will then be illustrated by referring to its preferred embodiments by way of the accompanying drawings. In FIG. 5 is shown a perspective view of a disposable diaper 1 as the absorbent article. FIGS. 6 to 8 are cross sections of the disposable diaper 1 taken along X—X line, Y—Y line and Z—Z line, respectively.

The disposable diaper 1 according to this embodiment has a liquid permeable topsheet 2, a liquid impermeable leakproof sheet 3, and a liquid retentive absorbent member 4 interposed between the sheets 2 and 3 as shown in FIGS. 5 to 8. A pair of fastening tapes 11 are provided on both sides (B1, B2) of the rear waist portion B.

In detail, as shown in FIGS. 5 to 8, the disposable diaper 1 according to this embodiment comprises an absorbent member 4, a leakproof sheet 3 which is approximately of the same size as the absorbent member 4, and a topsheet 2 which is disposed to cover the upper surface and both sides of the absorbent member 4. An outer nonwoven fabric layer 5 is disposed on the outer side of the leakproof sheet 3. A water-repellent nonwoven fabric strip 61 is provided on the topsheet 2 on both sides of the absorbent member 4 to form upstanding gathers 6. Both the outer nonwoven fabric layer 5 and the water-repellent nonwoven fabric strip 61 extend laterally from each side of the absorbent member 4, and leg elastic members 71 are held therebetween at the extension to form a pair of leg gathers 7. The free end 62 of each water-repellent nonwoven fabric strip 61 has an elastic member 63 to form upstanding gathers 6. The outer nonwoven fabric layer 5 and the topsheet 2 both extend from the longitudinal ends of the disposable diaper 1 to form a pair of waist portions 8. The waist portions 8 each has a waist elastic member 81 of band form sandwiched between the extended topsheet 2 and the extended outer nonwoven fabric layer 5. The absorbent member 4 is composed of bulky nonwoven fabric 41 holding an absorbent polymer 42 in the interstices among the constituent fibers and supporting paper 43 wrapping the bulky nonwoven fabric 41. The outer nonwoven fabric layer 5 has on the front waist portion A thereof a landing tape 51 on which the fastening tapes 11 are to be fixed.

The disposable diaper has the above-described compression recovery sheet in a prescribed position as a cushioning member.

The compression recovery sheet can be disposed between the leakproof sheet and the absorbent member, between the topsheet and the absorbent member, or inside the absorbent member. It may be disposed in two or more of these positions. Having the compression recovery sheet in this way, the disposable diaper is light and thin in a package and restores its thickness when taken out of the package for use. In this particular embodiment shown in FIGS. 6 to 8, the compression recovery sheet 44 is arranged between the leakproof sheet 3 and the absorbent member 4.

The compression recovery sheet 44 is preferably fixed in the prescribed position with an adhesive. The adhesive is applied to substantially the entire surface of at least one side of the compression recovery sheet 44 or substantially the entire contact surface of a member to be brought into contact with the compression recovery sheet 44 (i.e., the moisture-permeable leakproof sheet, the supporting paper containing the absorbent member, the topsheet, and the like, hereinafter referred to as a contact member) substantially uniformly in such a manner as to provide coated parts and uncoated parts. Thus, while retaining breathability of the disposable diaper, the recovery function possessed by the compression recovery sheet 44 directly acts on the disposable diaper, that is, the fixed compression recovery sheet 44 is compressed to make the disposable diaper compact in a package and allowed to expand on use to give a user a feeling of assurance. In addition, wrinkles, which may have occurred in non-adhered parts particularly in the contact member side, and resultant impairment of appearance are prevented.

The adhesive which can be used include rubber adhesives, such as solvent type rubber adhesives, emulsion type rubber adhesives, hot-melt type rubber adhesives; olefin adhesives such as hot-melt type olefin adhesives; and acrylic adhesives, such as solvent type acrylic adhesives and emulsion type acrylic adhesives.

The rubber adhesives are prepared by blending an elastomer as a base polymer with a tackifier and a softener.

The elastomer includes styrene-butadiene rubber (SBR), a styrene-butadiene-styrene block copolymer (SBS), a styrene-isoprene-styrene block copolymer (SIS), a styrene-ethylene-butylene-styrene block copolymer (SEBS), a styrene-ethylene-propylene-styrene block copolymer (SEPS), natural rubber, and synthetic isoprene rubber.

The tackifier includes $C_5$ cut petroleum resins, $C_9$ cut petroleum resins, dicyclopentadiene petroleum resins, rosin petroleum resins, polyterpene resins, terpene phenol resins, and hydrogenation products of these resins. Useful commercially available tackifiers include hydrogenated terpene resins such as Clearon (tradename: available from Yasuhara Kagaku K.K.), and hydrogenated aromatic petroleum resins such as Alcon (tradename: available from Arakawa Kagaku K.K.).

The softeners include process oils, mineral oils, various plasticizers, polybutene, and liquid tackifying resins each having a softening point of 10° C. or lower and an average molecular weight of 200 to 700. Specific examples of useful softeners include paraffinic oils, such as Shell Flex (tradename: available from Shell Chemical Company) and PW-90 (tradename: available from Idemitsu Kosan), and ester oils, such as tetraoctyl pyromellitate, didodecyl phthalate, and trioctyl trimellitate.

The solvent type rubber adhesives are prepared by dissolving the above-mentioned components in an organic solvent such as toluene, ethyl acetate and heptane. The emulsion type rubber adhesives are prepared by dispersing the above-described components in water. The hot-melt type rubber adhesives are prepared by melt blending the above-mentioned components. The hot-melt type rubber adhesives can contain antioxidants in order to prevent deterioration of these components by the heat of melt blending. Suitable antioxidants include phenol antioxidants, amine antioxidants, phosphorus antioxidants, and benzimidazole antioxidants.

Where the hot-melt type rubber adhesive is used, the elastomer as a base polymer is preferably used in an amount of 10 to 100 parts by weight per 100 parts by weight of the total amount of the tackifier and the softener.

The tackifier and the softener are preferably used in an amount of 50 to 90 parts by weight and 10 to 50 parts by weight, respectively, totally amounting to 100 parts by weight. The antioxidant is preferably added in an amount of 0.5 to 3 parts by weight per 100 parts by weight of the total amount of the elastomer, the tackifier, and the softener.

The hot-melt type olefin adhesives can be made solely of an amorphous poly-α-olefin (hereinafter APAO) or can be prepared by melt blending APAO with the same tackifier, the same softener and the same antioxidant as used in the above-described hot-melt type rubber adhesives. APAO includes a propylene-ethylene copolymer, a propylene-butene-1 copolymer, and a propylene-hexene copolymer, which are commercially available under tradenames Ubetac (supplied by Ube Rexene Co., Ltd.) and East Flex (available from Eastman Kodak Co.). APAO also includes a propylene-ethylene-butene-1 terpolymer, which is commercially available under a tradename Best Plast (supplied from Hultz).

The acrylic adhesives are prepared by copolymerizing a main monomer, a comonomer, and a functional group-containing monomer. The main monomer includes ethyl acrylate, butyl acrylate, and 2-ethylhexyl acrylate. The comonomer includes vinyl acetate, acrylonitrile, acrylamide, methyl methacrylate, and methyl acrylate. The functional group-containing monomer includes maleic anhydride, acrylic acid, and methacrylic acid. The solvent type acrylic adhesives are prepared by homogeneous polymerization of the monomer mixture in an organic solvent, such as toluene, ethyl acetate, and heptane. The emulsion type acrylic adhesives are prepared by emulsion polymerization of the monomer mixture in water.

Of the aforementioned various types of adhesives, preferred are hot-melt type adhesives, i.e., hot-melt type rubber adhesives and hot-melt type olefin adhesives in consideration of the use for absorbent articles and of the productivity. The hot-melt type rubber adhesives, which exhibit high adhesive strength, are particularly preferred. The hot-melt adhesive can be applied either in a contact system in which a hot-melt coater head is in contact with an adherend (i.e., a nonwoven fabric or a contact member), exemplified by slot coating or porous coating; or in a non-contact system in which the adhesive is atomized, exemplified by slot spraying, curtain spraying, melt-blowing or spiral spraying. The non-contact system is preferred because of less damage to the adherend and uniformity in making coated parts.

It is preferred for the hot-melt adhesive used to have a melt viscosity of 10,000 mPa·s or less, particularly 1,000 to 8,000 mPa·s, especially 1,000 to 6,000 mPa·s, at 180° C. Where the hot-melt adhesive is applied in an atomized state in a non-contact system, uneven coating or dripping can be prevented as long as it has a melt viscosity of 20 10,000 mPa·s or less.

The configuration of the coated parts with the adhesive includes, but is not limited to, spots, lines, dots, and spirals, which are preferred for uniformly fixing the compression recovery sheet 44 while securing breathability.

A preferred area ratio of the coated parts to the uncoated parts in the compression recovery sheet 44 is 2/8 to 7/3, particularly 3/7 to 6/4. It is preferred that the coated parts be uniformly distributed over the contact area of the compression recovery sheet 44 or the contact member.

Where the coated parts are spots, each spot preferably has a diameter of 0.3 to 2 mm, particularly 0.5 to 1 mm, and the density of the spots is preferably 9 to 400, particularly 25 to 100, per $cm^2$. Where the coated parts are lines, each line preferably has a thickness of 0.01 to 0.5 mm, particularly 0.05 to 0.1 mm. The density of the lines is preferably 10 to 40, particularly 10 to 30, per centimeter of a straight line drawn at right angles with an arbitrarily chosen line of the applied adhesive. Where the coated parts are dots, the dot density is preferably 9 to 400, particularly 25 to 100, per $cm^2$. Where the coated parts are spirals, the thickness of the spiral is preferably 0.05 to 1 mm, particularly 0.1 to 0.5 mm.

The above-described adhesive is preferably applied in an amount of 1 to 30 $g/m^2$, particularly 3 to 10 $g/m^2$, to secure improved adhesion of the compression recovery sheet 44 and to prevent blocking due to oozing of the above-described adhesive or dripping.

Materials forming the other members constituting the disposable diaper 1 having the above-described structure are briefly explained. The topsheet, the absorbent member, the water-repellent nonwoven fabric, and the outer nonwoven fabric can be of any materials generally employed in disposable diapers with no particular restrictions. The elastic members used in the leg portions, the upstanding gathers, and the waist portions can also be of any materials generally used in disposable diapers with no particular restrictions. The fastening tapes include a tape coated with an adhesive and a male member of a mechanical fastener. The landing tape on which the fastening tapes are to be fixed includes a release tape (used in combination with an adhesive tape) and a female member of the mechanical fastener (used in combination with the male member).

The leakproof sheet used in the disposable diaper is preferably a moisture permeable sheet. The moisture permeable leakproof sheet preferably has a moisture permeability of 0.5 to 4 g/(100 $cm^2$·hr), particularly 1.0 to 2.5 g/(100 $cm^2$·hr). With such a moisture permeability, creation of a humid internal environment and the resultant skin irritation can be prevented sufficiently while maintaining resistance against leakage of waste liquids such as urine. The moisture permeability as specified above is the value measured in accordance with JIS Z0208.

The moisture permeability. as described in JIS Z0208 can be summarized as follows: The water vapor transmission rate is the quantity of vapor passing through the unit area of filmy substance for the definite hour. In this standard, when constituting the boundary surface by the moisture-proof packaging materials at the temperature. of 25° C. or 40° C., and keeping the air of one side at a relative humidity of 90% and the air of the other side at the dry state by moisture absorbent, the value having converted the mass (g) passing through this boundary surface for 24 h into the value per 1 $m^2$ shall be defined as the water vapor transmission rate. The water vapor transmission rate can be calculated from the following formula on each test specimen and rounded off to significant figures as specified in JIS Z8401.

$$\text{Water vapor transmission rate:} (g/m^2 \cdot 24h) = (240 \times m)/t \cdot s$$

where
  s: area of the water vapor transmission (cm2)
  t: total of time intervals between the last two weighings (h)
  m: total of increased masses between the last two weighings (mg).

In order to give a user an enhanced feeling of assurance, it is preferable that the thickness of the disposable diaper according to the present embodiment under a pressure of 17.6 kPa (corresponding to a load of 180 gf/cm$^2$) and the thickness of the same diaper after unloading (no-load thickness) are such that the latter is 1.3 times or greater, particularly 1.5 to 3 times, the former (this ratio will hereinafter be referred to as a thickness ratio). Such a preferred thickness ratio is easily obtained by the use of the compression recovery sheet 44.

The thickness under load and the no-load thickness are measured according to the following methods. The absorbent article is unfolded flat, and a test piece having a width of 100 mm parallel to the lateral direction and a length of 100 mm parallel the longitudinal direction of the article is cut out, the center of the test piece agreeing with the intersection of a line longitudinally dividing the article into two equal pieces and a line laterally dividing the article into two equal pieces. Where the longitudinal or lateral size of the absorbent article is smaller than 100 mm, the size of the absorbent article could be the size of the test piece. The test piece is placed on a horizontal mount and allowed to stand for 24 hours with no load applied. Then, an acrylic resin plate and a weight are put thereon, and the test piece is further allowed to stand under the load for 24 hours. The weight and size of the weight are decided so as to give the test piece a total load of 180 gf/cm$^2$ together with the acrylic resin plate. The acrylic resin plate used was 100 mm wide, 100 mm long, and 5 mm thick. After 24-hour load application, the thickness of each corner of the test piece under load is measured (measurement 1) to obtain an average thickness of the four corners, which is taken as a thickness under a load of 17.6 kPa. The weight and the acrylic resin plate are removed, and the test piece is left to stand with no load applied. After 30 minute standing, an acrylic resin plate and a weight giving a total load of 98 Pa (corresponding to 1 g/cm$^2$) are placed thereon to flatten the test piece because any warpage or distortion of the test piece would hinder accurate thickness measurement. The weight and size of the weight used are decided so as to give the test piece a total pressure of 98 Pa together with the acrylic resin plate. The acrylic resin plate used was 100 mm wide, 100 mm long, and 5 mm thick. Immediately after putting the acrylic resin plate and the weight, the thickness of the test piece is measured in the same manner as in the measurement 1, and the average of the measured values of the four corners is taken as a no-load thickness.

Figure 9A:
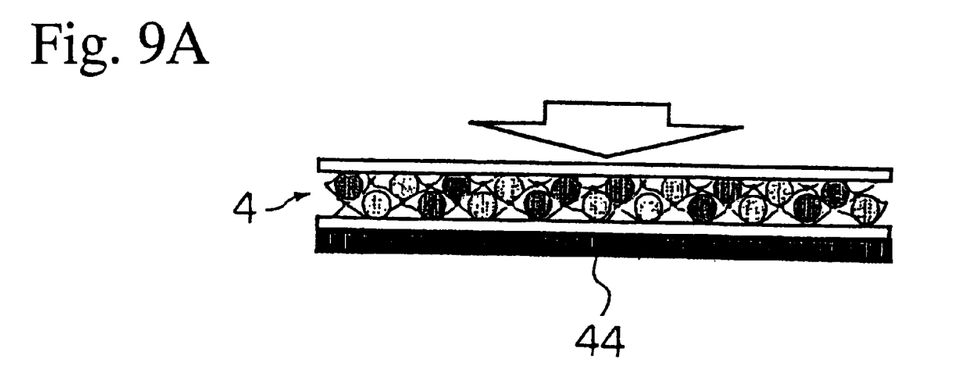
FIG. 9A and FIG. 9B each schematically illustrate the cross section of an embodiment of a disposable diaper as an absorbent article according to the present invention.
Figure 9B:
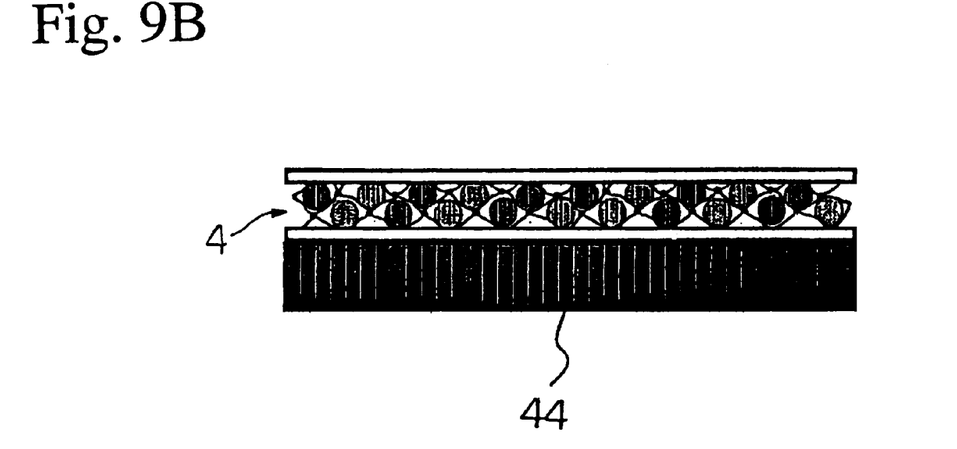

In packaging the disposable diapers according to the present embodiment, they are folded, stacked, compressed and packaged in a conventional manner. The disposable diaper in the packaged state (i.e., under some load) can be made thin (see FIG. 9A; the arrow shows the load-applying direction) equally to that of the one having nonwoven fabric that does not have the compressive recovery specified in the present invention but, upon being taken out of the package for use, restores its original thickness before compression owing to the compression recovery sheet 44 used as a cushioning member thereby to gain a necessary thickness for use, giving a user assuring feeling (see FIG. 9B).

Constructed as described above, the disposable diaper of the present embodiment can be made thinner and more compact in a packaged state and, when taken out of the package for use, increases in thickness moderately. Therefore, the user can use the disposable diaper without feeling unreliability on account of lack of thickness. Further, the disposable diaper maintains moisture permeability.

The present invention will now be illustrated in greater detail with reference to Examples. The following Examples are presented as being exemplary of the present invention and should not be considered as limiting.

EXAMPLES 1 TO 6 AND COMPARATIVE EXAMPLES 1 TO 4

A nonwoven fiber web (fiber aggregate) was formed by using the fibers shown in Tables 1 and 2 below by the method shown in Table 2 and heat treated at 200° C. to prepare a flat compression recovery sheet. The fiber composition, elastomeric component content, basis weight, no-load thickness, and compressive recovery of the resulting sheet are shown in Table 2. The sheets of Examples 2 and 6 were embossed by passing through matched-steel emboss rolls at 130° C. to obtain sheets having a large number of regularly arrayed bosses as shown in FIG. 4. In Example 2, the number of bosses per cm$^2$ (the projected area) was 2, the pitch K of the bosses was 7.5 mm, and the thickness M (the distance between the face and the back of the compression recovery sheet) was 0.5 mm. In Example 6, the number of bosses per cm$^2$ (the projected area) was 5, the pitch K of the bosses was 4.5 mm, and the thickness M was 0.5 mm.

TABLE 1

| | Fiber | | Core | Sheath | Core-sheath Weight Ratio | Fineness (denier) | Fiber Length (mm) | Fiber Configuration | Crimp Form |
|---|---|---|---|---|---|---|---|---|---|
| A | conjugate | elastomeric fiber | PBT | polyester elastomer | 6/4 | 3 | 51 | eccentric core-sheath | helical |
| B | conjugate | elastomeric fiber | PET | polyester elastomer | 5/5 | 3 | 51 | eccentric core-sheath | helical |
| C | conjugate | elastomeric fiber | PP | random polypropylene copolymer (70%) + metallocene-catalyzed LDPE (30%) | 5/5 | 5 | 44 | core-sheath | two-dimensional |
| D | conjugate | non-elastomeric fiber | PET | PE | 5/5 | 2 | 51 | core-sheath | two-dimensional |
| E | conjugate | non-elastomeric fiber | PP | PE | 5/5 | 3 | 51 | core-sheath | two-dimensional |
| F | single | | | PET | — | 5 | 76 | hollow | helical |
| G | single | | | PP | — | 3 | 44 | solid | two-dimensional |

Note:
PBT: polybutylene terephthalate
PET: polyethylene terephthalate
PP: polypropylene TABLE 1-continued

| Fiber | Core | Sheath | Core-sheath Weight Ratio | Fineness (denier) | Fiber Length (mm) | Fiber Configuration | Crimp Form |
|---|---|---|---|---|---|---|---|

LDPE: low-density polyethylene
PE: polyethylene

TABLE 2

| | Fiber Composition of Fiber Aggregate | Elastomeric Component Content (wt %) | Method of Fabrication | Embossing | Basis Weight (g/m²) | Thickness (mm) | Compressive Recovery (%) |
|---|---|---|---|---|---|---|---|
| Example | | | | | | | |
| 1 | A (70%)/F (30%) | 28 | | undone | 60 | 2.3 | 90 |
| 2 | A (70%)/F (30%) | 28 | | done | 60 | 2.5 | 95 |
| 3 | B (100%) | 50 | | undone | 50 | 1.8 | 85 |
| 4 | B (70%)/F (30%) | 35 | | undone | 50 | 2.2 | 90 |
| 5 | C (70%)/F (30%) | 10.5 | | undone | 60 | 1.9 | 70 |
| 6 | C (70%)/G (30%) | 10.5 | air-through | done | 60 | 2.3 | 80 |
| Comparative Example | | | | | | | |
| 1 | D (70%)/F (30%) | 0 | | undone | 50 | 2.1 | 55 |
| 2 | E (70%)/F (30%) | 0 | | undone | 50 | 1.7 | 55 |
| 3 | F (100%) | 0 | | undone | 50 | 1.2 | 50 |
| 4 | polypropylene (2.5 denier) | 0 | spun-bond | undone | 40 | 0.4 | 80 |

EXAMPLES 17 TO 12 AND COMPARATIVE EXAMPLES 5 TO 8

A disposable diaper shown in FIGS. 5 to 8 was made in a conventional manner by using conventional members except that a bulky nonwoven fabric having an absorbent polymer held in the interstices thereof which was enveloped in supporting paper was used as an absorbent member and that each of the compression recovery sheets prepared in Examples 1 to 6 and Comparative Examples 1 to 4 was disposed as a cushioning member between the absorbent member and the leakproof sheet. The thickness under load and no-load thickness of the resulting diaper were measured according to the above-described methods. The diapers were packaged in a usual manner and, after 24-hour standing, taken out of the package and evaluated for the thickness felt according to the following rating system. The results obtained are shown in Table 3 below.

Standard of Evaluation

A . . . The diaper feels sufficiently thick to give a very assuring feeling.
B . . . The diaper feels sufficiently thick to give an assuring feeling.
C . . . The diaper feels slightly thin to give a slightly unassuring feeling.
D . . . The diaper feels thin to give an unassuring feeling.

TABLE 3

| | | Compression Recovery Sheet | Diaper Thickness (mm) | | Assuring Feeling |
|---|---|---|---|---|---|
| | | | Under Load | No-load | |
| Example | 7 | Example 1 | 2.9 | 5.0 | A |
| | 8 | Example 2 | 2.8 | 5.2 | A |

TABLE 3-continued

| | | Compression Recovery Sheet | Diaper Thickness (mm) | | Assuring Feeling |
|---|---|---|---|---|---|
| | | | Under Load | No-load | |
| | 9 | Example 3 | 2.8 | 4.8 | B |
| | 10 | Example 4 | 2.7 | 4.8 | A |
| | 11 | Example 5 | 2.8 | 4.5 | B |
| | 12 | Example 6 | 2.8 | 4.9 | A |
| Comparative Example | 5 | Compara. Example 1 | 3.0 | 3.8 | C |
| | 6 | Compara. Example 2 | 2.8 | 3.6 | D |
| | 7 | Compara. Example 3 | 2.8 | 3.3 | D |
| | 8 | Compara. Example 4 | 3.0 | 3.5 | D |

EXAMPLES 13 TO 15 AND COMPARATIVE EXAMPLES 9 AND 10

(1) Preparation of Nonwoven Fabric

A fiber aggregate web was formed by carding using polyethylene terephthalate fiber having a thickness of 6.7 dtex and a length of 51 mm. An emulsion type acrylic ester adhesive shown in Table 4 below (all the adhesives shown in Table 4 are commercially available from National Starch and Chemical Corp.) was sprayed to the resulting web in the amount shown and dried at 160° C. to produce a compression recovery sheet comprising resin-bonded nonwoven fabric. In Comparative Example 10 no adhesive was applied.

TABLE 4

| | Emulsion Type Acrylic Ester Adhesive | Evaporation Residue (wt %) | Tg (° C.) | Coating Weight (g/m$^2$) |
|---|---|---|---|---|
| Example 13 | Nacrylic 125-4445 | 45 | −42 | 11.4 |
| Example 14 | Nacrylic 125-4280 | 50 | −4 | 14.6 |
| Example 15 | Yodosol AA-936 | 45 | −4 | 13.9 |
| Comparative Example 9 | Yodosol AA-35 | 45 | 20 | 9.8 |
| Comparative Example 10 | — | — | — | 0 |

(2) Preparation of Disposable Diaper

A disposable diaper shown in FIGS. 5 through 8 was prepared. A hot-melt adhesive compounded from the components shown in Table 5 below, whose melt viscosity is also shown in Table 5, was applied in an amount of 5 g/m$^2$ to the resin-bonded nonwoven fabric prepared above by spiral spraying at a hot air temperature of 150° C. under a spray pressure of 176.4 kPa. The adhesive-applied resin-bonded nonwoven fabric was adhered to supporting paper enclosing an absorbent member. A disposable diaper was prepared in a conventional manner using conventional materials. Comparative Example 10 is equivalent to Example 1 of Japanese Patent Laid-Open Publication No. 1-285265.

TABLE 5

| Hot-Melt Adhesive | | | |
|---|---|---|---|
| Composition | Base polymer | SIS[*1] | 20 wt % |
| | Tackifier | Hydrogenated terpene resin[*2] | 65 wt % |
| | Softener | Process oil[*3] | 15 wt % |
| | Antioxidant | Hindered phenol[*4] | 0.3 wt % |
| Melt viscosity[*5] (180° C.) (mPa · s) | | | 2000 |

Note:
[*1]Krayton D1117, available from Shell Chemical Company
[*2]Clearon P105, available from Yasuhara Chemical Co., Ltd.
[*3]PW-90, available from Idetmitsu Petrochemical Co., Ltd.
[*4]Irganox 1010, available from Chiba Geigy, Ltd.
[*5]Measured with a B type viscometer supplied by Tokyo Keiki K.K.

(3) Evaluation of Performance

In Table 6 are shown the basis weight, initial thickness (thickness before compression), and compressive recovery of the resin-bonded nonwoven fabric used in Examples 13 to 15 and Comparative Examples 9 and 10, and the thickness under load, no-load thickness, and thickness ratio (ratio of no-load thickness to the thickness under load) of the disposable diaper having the resin-bonded nonwoven fabric.

TABLE 6

| | Compression Recovery Sheet | | | Disposable Diaper | | |
|---|---|---|---|---|---|---|
| | | | | Thickness (mm) | | |
| | Basis Weight (g/m$^2$) | No-load Thickness (mm) | Compressive Recovery (%) | Under-Load | No-load | Thickness Ratio |
| Example 13 | 74.9 | 2.73 | 90.1 | 3.0 | 5.1 | 1.70 |
| Example 14 | 77.1 | 2.42 | 88.4 | 2.9 | 5.1 | 1.76 |
| Example 15 | 76.5 | 2.68 | 70.0 | 3.0 | 4.4 | 1.47 |
| Comparative Example 9 | 75.7 | 2.78 | 53.6 | 3.0 | 3.8 | 1.27 |
| Comparative Example 10 | 80 | 5.20 | 58.0 | 3.0 | 3.8 | 1.27 |

As is apparent from Table 6, the disposable diapers of Examples 13 to 15 having the specific compression recovery sheet disposed in a prescribed position can be made compact when compressed and restore the thickness on being relieved. In particular, it is seen that the compression recovery sheet comprising resin-bonded nonwoven fabric formed by using an adhesive having a low Tg achieves an extremely high compressive recovery.

The compression recovery sheet according to the present invention is thin under some load and increases its thickness when the load is removed so that it provides thin and compact absorbent articles such as disposable diapers and sanitary napkins in a package which, on being taken out of the package for use, gains a thickness necessary as an absorbent article to make a user feel assured.

The absorbent article according to the present invention is compact in a packaged state and increases its thickness on being taken out of the package to make a user feel assured in use. Further, the absorbent article of the present invention maintains moisture permeability.

The invention having been thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A compression recovery sheet which comprises a fiber aggregate, said fiber aggregate comprising a conjugate fiber, wherein said conjugate fiber comprises an elastomeric component and a non-elastomeric component, wherein said fiber aggregate contains 10 to 90% by weight of the elastomeric component, wherein said compression recovery sheet has a basis weight of 15 to 100 g/m$^2$, a no-load thickness of 1 to 10 mm, a compressive recovery of 60% or more, and has 1 to 100 bosses per cm$^2$ of a projected area thereof at a pitch of 1 to 20 mm, wherein one side of said compression recovery sheet has a large number of said bosses regularly arrayed and the reverse side of said compression recovery sheet contains the corresponding depressions from said regularly arrayed bosses of said one side wherein the contour of said one side and that of said reverse side are substantially the same, said bosses, which are formed by use of a matched pair of relief engraved rolls, form an uneven pattern on said compression recovery sheet, and said conjugate fiber has said non-elastomeric component as a core of the conjugate fiber and said elastomeric component is an outer sheath around said core.

2. A compression recovery sheet according to claim 1, wherein said fiber aggregate contains 10% by weight or more of crimped fibers of helical form.

3. The compression recovery sheet according to claim 2, wherein the crimped fibers of helical form have 3 to 20 crimps per inch.

4. A process for producing the compression recovery sheet of claim 1, comprising:
   a) heat treating a fiber aggregate web to form a fiber aggregate sheet, and
   b) heat roll processing said fiber aggregate sheet by means of a relief engraved roll to produce said compression recovery sheet.

5. The compression recovery sheet according to claim 1, wherein said elastomeric component further comprises a polyester or a low density polyethylene produced by polymerization in the presence of a metallocene catalyst.

6. The compression recovery sheet according to claim 5, wherein said fiber aggregate contains conjugate fibers comprising said elastomeric component containing said polyester or said low density polyethylene and a non-elastomeric component.

7. The compression recovery sheet according to claim 1, wherein the conjugate fibers are bonded to each other by thermal fusion, and the conjugate fibers have a thickness of 1 to 15 denier.

8. The compression recovery sheet according to claim 1, wherein:
   the elastomeric component is at least one selected from the group consisting of polyester, low density polyethylene and 70%/30% random polypropylene copolymer/metallocene-catalyzed LDPE; and
   the non-elastomeric component is at least one selected from the group consisting of polyethylene terephthalate, polybutylene terephthalate, polyethylene, polypropylene, nylon and acrylic resin.

9. An absorbent article comprising a liquid permeable topsheet, a liquid-impermeable leakproof sheet, a liquid retentive absorbent member interposed between said topsheet and said leakproof sheet and, as a cushioning member, the compression recovery sheet of claim 1.

10. An absorbent article according to claim 9, wherein said compression recovery sheet is disposed between said leakproof sheet and said absorbent member, between said topsheet and said absorbent member, or inside said absorbent member, or at a plurality of these positions.

11. A compression recovery sheet comprising a resin-bonded non-woven fabric substantially comprising synthetic fiber and having been impregnated or coated with an adhesive whose glass transition temperature is 4° C. or lower and has a basis weight of 15 to 100 g/m$^2$, a no-load thickness of 1 to 10 mm, and a compressive recovery of 60% or more,
   wherein said synthetic fiber comprises polypropylene or polyethylene terephthalate, and
   said resin-bonded non-woven fabric is prepared by impregnating or coating an unbonded fiber aggregate with said adhesive followed by a heat treatment.

12. A compression recovery sheet according to claim 11, wherein said adhesive is an emulsion type adhesive comprising an acrylic ester as a base polymer.

13. A compression recovery sheet according to claim 11, which contains said adhesive in an amount of 10 to 60% by weight based on the weight of said compression recovery sheet.

14. An absorbent article comprising a liquid permeable topsheet, a liquid-impermeable leakproof sheet, a liquid retentive absorbent member interposed between said topsheet and said leakproof sheet and, as a cushioning member, the compression recovery sheet of claim 11.

15. The absorbent article according to claim 14, where said compression recovery sheet is disposed in at least one of:
   a) between said leakproof sheet and said absorbent member,
   b) between said topsheet and said absorbent member, or
   c) inside said absorbent member.

16. The absorbent article according to claim 15, wherein said leakproof sheet is a moisture permeable sheet having a moisture permeability of 0.5 to 4 g/(100 cm$^2$·hr), and said compression recovery sheet is fixed at a prescribed position with an adhesive which has been applied to substantially the entire surface of at least one side of said compression recovery sheet or substantially the entire contact area of a member to be brought. into contact with said compression recovery sheet in such a manner that said adhesive is distributed substantially uniformly while providing applied parts and unapplied parts.

17. The absorbent article according to claim 16, wherein the leakproof sheet has a moisture permeability of 1.0 to 2.5 g/(100 cm$^2$·hr).

18. The compression recovery sheet of claim 11, wherein said adhesive has a glass transition temperature of –4° C. or lower.

* * * * *